United States Patent [19]

Mykkanen

[11] 4,373,175
[45] Feb. 8, 1983

[54] APPARATUS TO DISSIPATE STATIC ELECTRICITY

[75] Inventor: C. Fred Mykkanen, Fridley, Minn.

[73] Assignee: Honeywell Inc., Minneapolis, Minn.

[21] Appl. No.: 244,617

[22] Filed: Mar. 17, 1981

[51] Int. Cl.³ .......................... H05F 3/02; A61N 1/14
[52] U.S. Cl. ..................................... 361/220; 361/212
[58] Field of Search .............. 361/212, 220, 221, 222, 361/223, 224; 174/5 SB; 128/381, 384, 783, 802

[56] References Cited

U.S. PATENT DOCUMENTS

| | | | |
|---|---|---|---|
| 2,712,098 | 6/1955 | Legge | 361/223 |
| 3,084,700 | 4/1963 | Fischer et al. | 361/221 X |
| 3,857,397 | 12/1974 | Brosseau | 361/220 X |
| 4,313,148 | 1/1982 | Turner | 361/212 |

FOREIGN PATENT DOCUMENTS

| | | | |
|---|---|---|---|
| 637705 | 1/1964 | Belgium | 128/381 |
| 2547390 | 5/1977 | Fed. Rep. of Germany | 361/212 |

Primary Examiner—Reinhard J. Eisenzopf
Attorney, Agent, or Firm—Roger W. Jensen

[57] ABSTRACT

Safety apparatus connectible between a human and an electrically conductive terminal includes an electrical part connectible to the terminal, a first electrical cable having one end adapted for electrical connection to the human, and an electromechanical device interconnecting the opposite end of the cable and the electrical part, such electromechanical device including releasably interconnected plug and socket elements and an elongated flexible connection located between the elements and part, the elements being releasable in response to tension exertion transmitted between the cable and the flexible connection.

18 Claims, 3 Drawing Figures

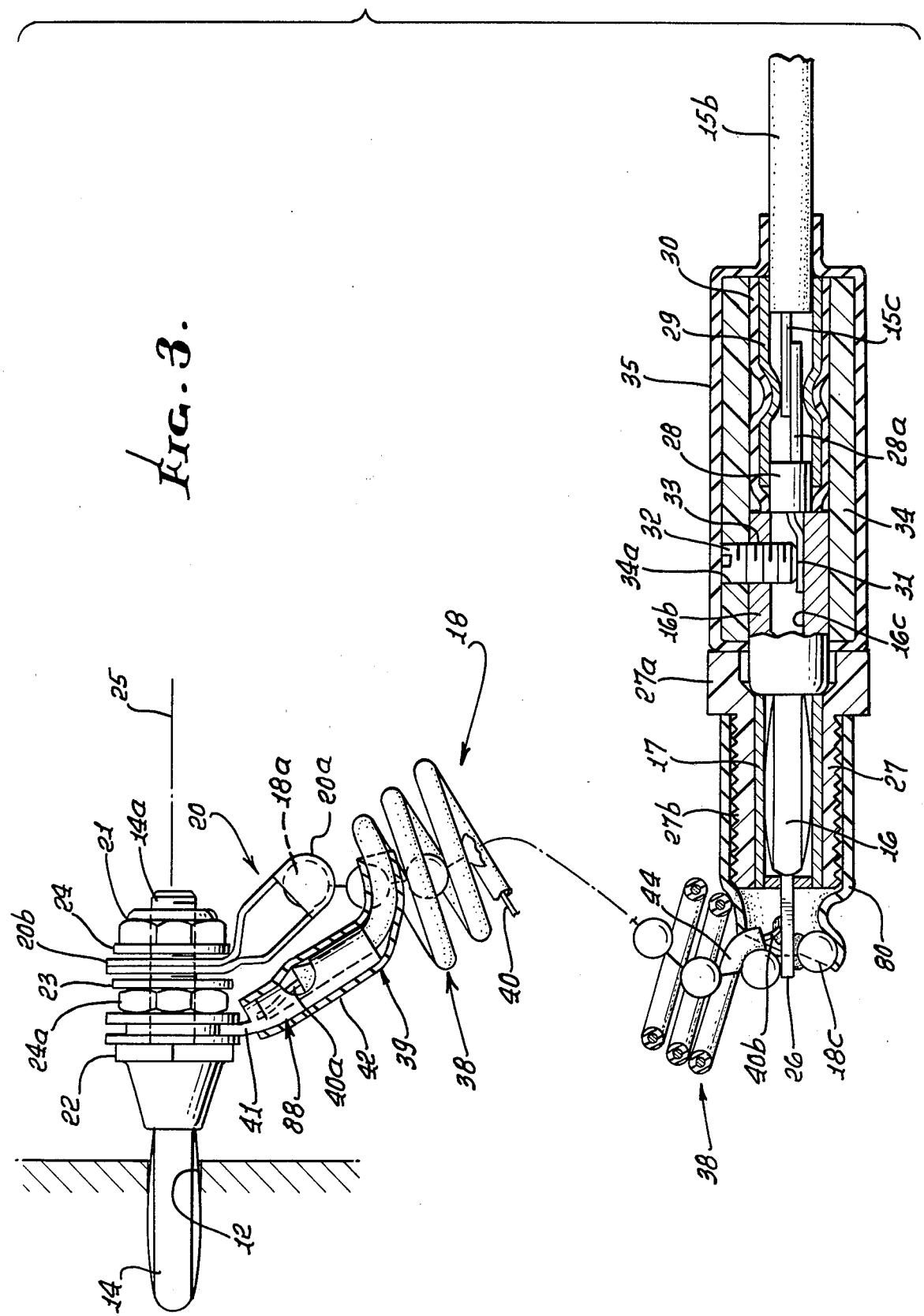

APPARATUS TO DISSIPATE STATIC ELECTRICITY

BACKGROUND OF THE INVENTION

This invention relates generally to devices used to prevent damage to electrostatic sensitive equipment; and more particularly it concerns personnel grounding, so-called "wrist straps" useful in such applications.

The problem of preventing damage to electrostatic sensitive equipment is a serious one. As an example, in fabrication of electronic as well as other apparatus employing plastic parts, the problem of unwanted and destructive static build-up and arcing, which can lead to damaged electronic equipment, shocks to employees and fires, is acute. In the past, grounding wires have been used to conduct electrostatic charge build-up on personnel handling electronic parts to grounded members, and for this purpose wrist straps were attached to the arms of users to conduct charge to the grounding wires. Problems encountered included inadvertent wire disconnection from the grounding member and from the wrist straps, as when a worker moves his arm as a way to tension the wire, and wire breakage. One expedient to counter this problem was to wind the wire around the wrist strap, or to tape the wire; however, this was found objectionable, one reason being that it interfered with good electrical contact between the wrist strap and the user's wrist. The cost of equipment damage and reduced worker efficiency due to such static build-up is extremely high.

SUMMARY OF THE INVENTION

It is a major object of the invention to provide simple, efficient apparatus which does not interfere with a worker's tasks, and which removes the static build-up problem. Such apparatus is connectible between a human being and an electrically conductive terminal, as for example a ground terminal, and comprises:

(a) an electrical part connectible to that terminal,
(b) a first electric cable having one end adapted for electrical connection to the human, as for example to his or her wrist,
(c) and means interconnecting the opposite end of the cable and the part, such means including releasable plug and socket elements and an elongated flexible connection located between the elements and the part, the elements being releasable in response to tension exertion transmitted between the cable and the flexible connection.

As will appear, the flexible connection may comprise a tension transmitting flexible bead chain; and a second electrical cable may be connected between one of the elements and the part to transmit electrical current, the second cable paralleling the chain. Typically, the second cable may extend about or coil about the chain, to protect it, and to be free of tension when the chain is tensioned.

Further, a protective electrical resistor may be connected in series with the described means that interconnects the cable and part, and may be protectively associated with one of two tension releasably intercoupled components that define a further electrical connection between the cable and the bead chain.

In addition, a releasable snap connection may be provided between the cable and a strap that is adapted to conductively connect to the human, as for example to his or her wrist.

These and other objects and advantages of the invention, as well as the details of an illustrative embodiment, will be more fully understood from the following description and drawings, in which:

DRAWING DESCRIPTION

FIG. 3 is a fragmentary view showing details of connections that may be employed in the FIG. 1 apparatus.

DETAILED DESCRIPTION

Figure 1:
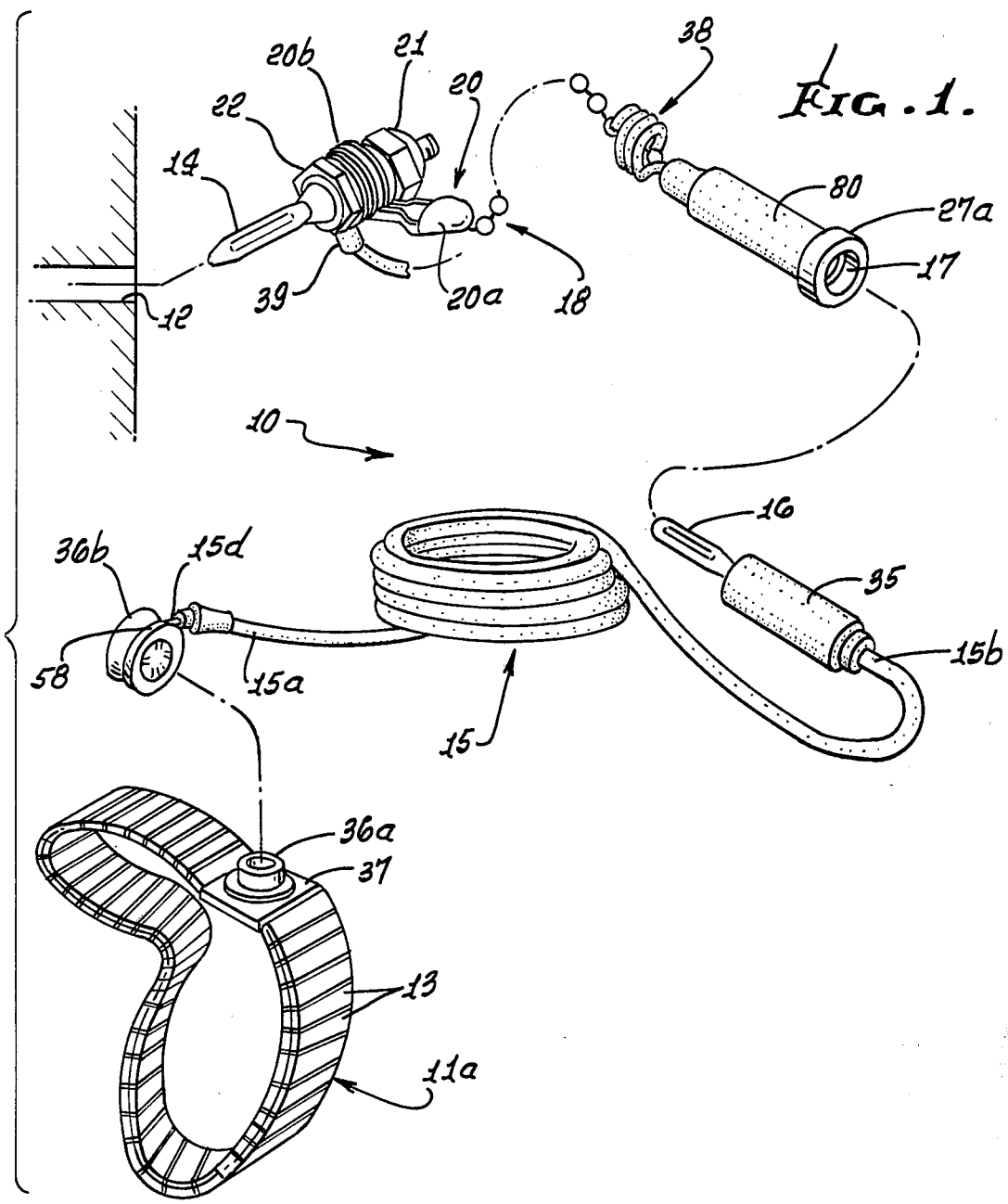
FIG. 1 is a perspective view of safety apparatus incorporating the invention.
Figure 2:
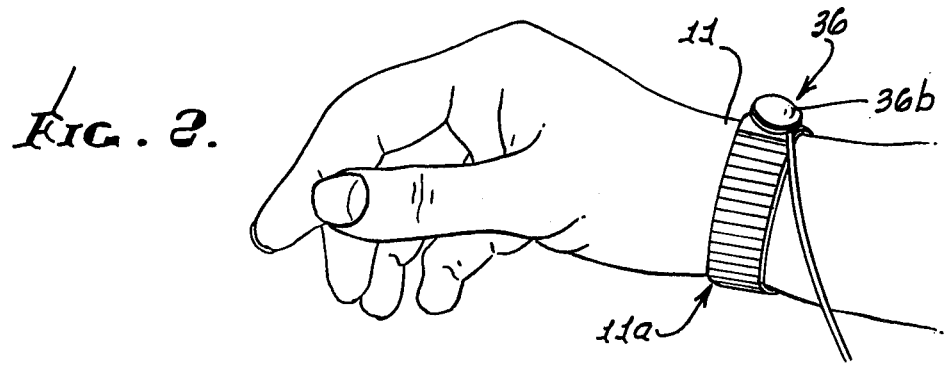
FIG. 2 is an elevation showing the manner in which the FIG. 1 apparatus may be connected to the wrist of a user.

In the drawings, the apparatus generally indicated at 10 is connectible between a human (as for example a wrist 11 shown in FIG. 2) and an electrically conductive terminal (as for example the grounding terminal or component 12 shown in FIG. 1). At one end of the apparatus, a conductive metal wrist strap 11a is well adapted to be easily emplaced on the wrist 11, for establishing good electrical contact therewith. The strap for example is expansible and comprises interconnected metallic links 13. At the opposite end of the apparatus, a conductive part such as "banana" plug 14 is well adapted to be easily and removably inserted into receptacle 12, to establish good electrical contact with same (as for example grounding contact).

The apparatus 10 generally includes, between strap 11a and plug 14, a first electrical cable, as for example insulated cable 15, having one end 15a adapted for electrical connection to the human (as via strap 11a); and means interconnecting the opposite end 15b of the cable and the part (such as plug 14). Such means includes releasably interconnected plug and socket elements at 16 and 17, and an elongated flexible connection, as for example at 18, located between the elements 16 and 17 and the plug 14. The interconnected elements 16 and 17 are quickly releasably (as by relative separation) in response to endwise tension exertion transmitted between the cable 15 and the flexible connection 18, as for example when a user's wrist or arm is for some reason displaced sufficiently away from the grounding terminal 12. Such separation can occur in response to tension exertion in any direction due to the flexibility of connection 18 and the flexibility of the cable 15, respectively extending endwise oppositely of the interconnected elements 16 and 17. This is to be contrasted with the relative insensitivity to tension exertion of plug 14 and fixed position terminal 12, their relative separation only occurring in response to tension exertion in one axial direction.

More specifically, the flexible connection 18 may advantageously comprise an electrically conductive, metallic bead chain as shown. One end 18a of the chain is swivel connected to the plug 14, as via a metallic part or coupler 20. The latter includes a receptacle 20a for the end bead 18a of the chain, and a washer 20b integral with receptacle 20a and loosely swiveled on an endwise extension 14a of the plug 14, and which may be threaded to receive stop nut 21. Located between stop nut 21 and flange 22 on the plug are two swiveled washers 23 and 24, the bead chain coupler end 20b being loosely confined between such parts. See also nut 24a. Accordingly, the worker-user is enabled to move his hands and arms freely, and the chain 18 will swivel about the axis 25 of plug 14 in response to such movement, without pulling the plug 14 from its grounding receptacle 12. Any static electricity carried by the user is dissipated via the apparatus to the terminal or receptacle 12.

The opposite end bead 18c of the chain is shown in FIG. 3 as soldered to a metallic post 26 integral with metallic socket element 17. Surrounding the latter is an insulative molded plastic sleeve or housing 27, having an end flange 27a. Sleeve 27 may be externally grooved or threaded at 27b to accept and retain a length of protective plastic tubing having a shrink fit over the sleeve and over the soldered connection of the bead 18c to post 26, as shown. Such tubing appears at 80.

The plug 16 has electrical connection with an electrical wire 15c projecting from the end of cable 15, as shown in FIG. 3, and typically via a protective electrical resistor 28, connected in series between 16 and 15c. The resistor protects against excessive current flow between elements 12 and 11a (should, for example, the wearer touch a high power source). A crimped sleeve 29 may be employed to connect wire 15c to wire 28a of the resistor, and a molded plastic sheath 30 may be fitted over the sleeve 29 and the resistor cylinder, as shown. The opposite end resistor wire 31 is shown as forcibly biased against the inner surface 16c of the plug extension 16b, as by a set screw 32 having threaded interconnection at 33 with the extension 16b. A molded plastic tubular housing 34 fits over the described elements, and has a side opening 34a receiving the head of the screw 32. A length of shrinkable plastic tubing 35 fits over the assembly as shown.

The opposite end 15a of the cable 15 is connected with the wrist strap 11a as via a snap connection seen at 36. It may for example include a metallic male snap part 36a integral with plate 37 of strap 11c, and a female part 36b having high reliability, radially crimped connection at 58 to an electrical wire 15d protruding from the insulative sheath of the cable. Release of the snap connection allows the worker-user to move about, free of the apparatus excepting for the wrist band.

In accordance with an important aspect of the invention, a second electrical cable is connected between one of the releasable elements 16 and 17 and the part or plug 14, to transmit electrical current between them while remaining in slack condition, i.e. free of tension when the bead chain 18 is swiveled and tensioned. As shown, the second cable 38 advantageously is loosely coiled about the bead chain 18, and includes an outer insulative sheath 39 covering an electrical wire 40. One end 40a of the wire is typically held clamped to the fitting 41 by crimping of terminal 88. Fitting 41 contains an opening to fit over and integrally connect with the plug extension 14a, providing positive electrical continuity. Coiled cable 38 flexes to accommodate swiveling of bead chain washer 20b. Terminal 88 affords both mechanical strain relief and electrical connection. Note the bending of part 20 beyond the stop nut 21, so that the bead chain and cable 38 may swivel free of interference with the nut 21. Insulative flexible tubing length 42 extends about the connection between wire end 40a and fitting 41.

The opposite end 40b of the wire 40 is soldered to the post 26 near the end bead 18c, and a length of insulative heat shrink sleeving 80 is shrunk over the connection as shown. Accordingly, a dual or parallel (redundant) electrical connection is made between plug 14 and socket 17, via flexible elements 18 and 38, at least one of the latter being tension transmitting, ensuring that electrical continuity is maintained, which enables release of the plug 16 from socket 17 in response to sufficient tension transmission (2–5 pounds). This provides a sensory feedback to the wearer indicating inadvertent disconnection.

The apparatus has the following additional advantages: it is comfortable to the wearer, attractive in appearance, and possesses electrically and mechanical integrity, and is non-hazardous. For example, the coiled cable 38 insulates the metallic bead chain 18 against contact with voltage sources. The swivel connections prevent sharp bends in the wire assembly in the event angular pull forces are applied. The device prevents accumulation of static charge on the body, while allowing freedom of movement, protection against dangerous electrical currents, and enables three possible quick break-away zones in emergencies, for operator protection.

I claim:

1. In safety apparatus connectible between a human and an electrically conductive terminal, the combination comprising
   (a) an electrical part connectible to said terminal,
   (b) a first electrical cable having one end adapted for electrical connection to said human,
   (c) means interconnecting the opposite end of the cable and said part, said means including releasably interconnected plug and socket elements and an elongated flexible connection located between said elements and said part, said elements being releasable in response to tension exertion transmitted between said cable and said flexible connection,
   (d) and a second electrical cable coiled about said flexible connection and connected between one of said elements and said part to transmit electrical current therebetween, and to be free of tension when the flexible connection is tensioned.

2. The combination of claim 1 wherein said flexible connection comprises a flexible bead chain.

3. The combination of claim 2 wherein said means includes a swivel connection between said bead chain and said part.

4. The combination of claim 3 wherein said part comprises a plug.

5. The combination of claim 4 including said terminal in the form of a receptacle receiving said plug for dissipating static electricity passing between the human and said part via said cable, said means and said chain.

6. The combination of claim 1 including an electrical resistor connected in series with said means.

7. The combination of claim 6 wherein said resistance is integral with one of said plug and socket elements.

8. The combination of claim 1 including a strap having a conductor adapted to engage the human body.

9. In safety apparatus connectable between a human and an electrically conductive terminal, the combination comprising:
   (a) an electrical part connectable to said terminal,
   (b) a first electrical cable having one end adapted for electrical connection to said human,
   (c) means interconnecting the opposite end of the cable and said part, said means including releasably interconnected electrical connector elements and an elongated flexible connection located between said elements and said part, said elements being releasable in response to tension exertion transmitted between said cable and said flexible connection, and (d) a second electrical cable connected between one of said elements and said part to transmit electrical current therebetween, said second cable being in slack condition.

10. The combination of claim 9 wherein said elongated flexible connection comprises a flexible bead chain.

11. The combination of claim 10 wherein said second electrical cable is coiled about said chain and is connected between one of said elements and said part to transmit electrical current therebetween, and to be free of tension when the chain is tensioned.

12. The combination of claim 10 wherein said interconnecting means includes a swivel connection between said bead chain and said part.

13. The combination of claim 12 wherein said part comprises a plug.

14. The combination of claim 13 including said terminal in the form of a receptacle receiving said plug for dissipating static electricity passing between the human and said part via said cable, said means and said chain.

15. The combination of claim 9 including an electrical resistor connected in series with said interconnecting means.

16. The combination of claim 15 wherein said resistance is integral with one of said electrical connector elements.

17. The combination of claim 9 including a strap having a conductor adapted to engage the human body.

18. The combination of claim 17 including a snap connection between said strap and said cable.

* * * * *